United States Patent [19]

Maas et al.

[11] 4,218,387

[45] Aug. 19, 1980

[54] PREPARATION OF CATALYTIC COPPER AND PRODUCTION OF ORGANOCHLOROSILANE USING SAID COPPER

[75] Inventors: Joachim Maas, Bergheim; Rudolf Mundil, Leverkusen; Bruno Degen, Bergisch-Gladbach; Hans-Heinrich Moretto, Cologne, all of Fed. Rep. of Germany

[73] Assignee: Bayer Aktiengesellschaft, Leverkusen, Fed. Rep. of Germany

[21] Appl. No.: 953,047

[22] Filed: Oct. 19, 1978

[30] Foreign Application Priority Data

Nov. 11, 1977 [DE] Fed. Rep. of Germany ....... 2750556

[51] Int. Cl.² ........................ B01J 23/72; C07F 7/16
[52] U.S. Cl. ................................... 556/412; 252/476
[58] Field of Search ............. 252/476; 260/448.2 T; 423/604

[56] References Cited

U.S. PATENT DOCUMENTS

| | | | |
|---|---|---|---|
| 2,383,818 | 8/1945 | Rochow et al. | 252/476 X |
| 2,420,540 | 5/1947 | Hubbell | 75/0.5 BC |
| 2,443,902 | 6/1948 | Ferguson et al. | 252/476 X |
| 2,464,033 | 3/1949 | Gilliam | 260/448.2 T |

FOREIGN PATENT DOCUMENTS 645314 10/1950 United Kingdom .............. 260/448.2 T

*Primary Examiner*—W. J. Shine
*Attorney, Agent, or Firm*—Sprung, Felfe, Horn, Lynch & Kramer

[57] ABSTRACT

In the preparation of catalytic copper with an average particle size between about 0.1 and 100 microns and a copper-I oxide content of about 3 to 100% by oxidation of a Cu powder, the improvement which comprises carrying out the oxidation with oxygen at a reduced partial pressure compared with that of air, the resulting catalyst being of enhanced catalytic activity especially for the reaction of hydrocarbon chlorides with silicon for the production of organochlorosilanes (Rochow synthesis) wherein the desired material is produced in higher yield and greater selectivity.

7 Claims, No Drawings

PREPARATION OF CATALYTIC COPPER AND PRODUCTION OF ORGANOCHLOROSILANE USING SAID COPPER

The present invention relates to a process for the preparation of catalytic copper which can be employed, in particular, in the reaction of hydrocarbon chlorides with silicon for the purpose of the production of organochlorosilanes (Rochow synthesis).

The types of copper suitable for carrying out the Rochow synthesis are prepared, inter alia, by electrolysis of a Cu salt solution, atomization of a Cu melt, mechanical comminution of coarse lumps of Cu or by precipitation of Cu from Cu salt solutions using appropriate reducing agents, it also being possible for baser metals, such as, for example, iron, to be used for the reduction of the copper ions (so-called cementation of copper).

U.S. Pat. Nos. 2,383,818 and 2,464,033 mention that, for example, doping with copper oxides catalyzes the Rochow synthesis, but without going into more detail with regard to the nature of the actual preparation of the oxide.

However, it is already known that such a doping has a very substantial influence on the course of the catalysis. Thus, commercially available $Cu_2O$ or $CuO$ catalyzes the Rochow synthesis far less than, for example, the catalyst prepared by the process according to the invention.

U.S. Pat. No. 2,420,540 describes the preparation of a copper-containing powder which, according to U.S. Pat. No. 2,443,902, can be successfully used as a catalyst in the Rochow synthesis of organochlorosilanes. This powder is a dendritic cement copper which is converted, on the surface, into copper oxides, preferably Cu-I oxide, by an oxidizing hot grinding process in the presence of a combustion gas/air mixture in a grinding installation.

This grinding process not only permits comminution of the cement copper down to the desired particle size of a few microns, but at the same time also generates the temperature used, of about 370° to 540° C., through a drying process for the wet cement copper containing about 10% of residual moisture.

However, the preparation, according to U.S. Pat. No. 2,420,540, of the Cu catalyst has the disadvantage that the composition of the combustion gas can vary, which leads to changing catalyst qualities. Reduced constituents of the gas, such as, for example, CO, in particular adversely influence the activity of the copper-containing powder formed. Varying moisture contents of the crude cement copper employed also contribute to variations in the quality of the catalysts produced.

A process has now been found for the preparation of a catalytic copper active in the Rochow synthesis, which is characterized in that Cu powder is after-oxidized at a reduced partial pressure of oxygen, compared with air, at temperatures between about 100° and 1,000° C.

Surprisingly, it has been found that the yield of dimethyldichlorosilane can be substantially improved when the oxidation process is carried out according to the invention, this effect being based on the increase of the dimethyldichlorosilane selectivity of the catalyst and/or on the rise in the yield of crude silane.

The process according to the invention is not only suitable for the after-oxidation of cement copper powders, but can be successfully used in the case of Cu powders of different origin.

Commercially available powders which have been produced, for example, by mechanical comminution of copper or by atomization of a Cu melt can be used as starting substances.

The electrolysis of Cu salt solutions, the reduction of copper salt solutions with suitable reducing agents or disproportionation reactions of Cu-I salts are also possible for the preparation of appropriate starting materials. The particle size of the product employed in the after-oxidation should preferably be between about 0.1 and 100 microns.

The oxidation is most easily carried out using nitrogen/air mixtures, the oxygen content of which is between about 0.1 and 15%, preferably between about 0.5 and 8%. It is also possible to use other gases which do not have a reducing action, such as, for example, $CO_2$ or a noble gas, instead of nitrogen. As is shown by example hereinbelow, the presence of gases such as CO or $H_2$, which can reduce the copper oxides formed during the oxidation process, have an adverse effect on the properties of the catalyst.

It is also possible to use pure oxygen, instead of air, as the source of oxygen.

The reduced partial pressure of oxygen can also be realized by using oxygen under a pressure of about 0.001 to 0.2 atmospheres absolute, without doping with a further gas.

The reaction temperature, partial pressure of oxygen and residence time of the copper in the reaction zone depend somewhat on one another in the process according to the invention. Thus, for example, as a rule the oxidation time at 100°–400° C. and under relatively high partial pressures is about 5 to 40 minutes, but is only a few seconds at 700°–1,000° C. Accordingly, a few seconds to a few minutes must be allowed for temperatures between 400° and 700° C.

At low partial pressures of oxygen, such as, for example, 0.002 or 0.02 atmospheres absolute, a longer treatment time must be reckoned with, even at high temperatures, in order to achieve the desired result.

An overall residence time for the copper powder in the oxidation zone is between about 2 seconds and 120 minutes which will result in a copper-I oxide content of about 3 to 100%.

The oxidation of the copper can be carried out in a suitable manner in a fluidized bed or stirred bed. However, it is also possible to pass a gas of the desired composition, charged with solid, through a hot reaction chamber, or to oxidize the powder through contact with heated gas.

In operating a fluidized bed or stirred bed, the settling speed of individual Cu particles can be exceeded by the gas streaming in, so that in general a separator (cyclone or filter) must be connected downstream from the reaction vessel.

It is absolutely essential to connect a cyclone downstream if it is necessary to separate solid/gas mixtures, such as are obtained in the short-time after-oxidation of Cu powders, for example in the hot tube.

Any agglomerates produced by the oxidation can be broken down by subsequent grinding, for example in a ball mill, pin disc mill or hammer mill.

It is also possible, for example, to carry out the process according to the invention directly in a heated hammer mill.

The catalytic activity of the catalysts is tested by reacting 20 g of a silicon (analysis: 98.40% of Si; 1.00% of Fe; 0.36% of Al; and 0.14% of Ca) having a particle size distribution as follows: <36 μm: (31.3%); 36–71 μm: (22.6%); 71–100 μm: (17.8%); 100–160 μm: (18.0%); and >160 μm (10.3), and 1.6 g of catalyst and 0.02 g of zinc (as a promoter) with 760 Nml/hour of $CH_3Cl$ in a laboratory fixed bed reactor under 2 atmospheres absolute and at 360°–280° C. In order to shorten the induction period, the reaction is allowed to start up at 360° C., and thereafter the temperature is lowered by 10° C. in each of the first two hours, and then by 15° C. per hour until the 280° C. mark is reached.

The laboratory fixed bed reactor is a cylindrical glass tube of 17 mm internal diameter and 350 mm length, which is provided with a vibrator and heater and into which methyl chloride is passed in, from the bottom, over the layered Si/Cu contact catalyst. A collecting vessel which is provided with a condenser and is coupled to the reactor is used for separating off the silanes produced. The resulting product is weighed and analyzed by gas chromatography.

The process according to the invention may be illustrated in more detail with the aid of the following examples.

Examples 1 and 2 show that by means of an after-oxidation, according to the invention, of the Cu using gas mixtures with a decreased oxygen content, compared with that of air, it is possible to increase the dimethyldichlorosilane selectivity of the catalyst, with respect to the non-treated Cu powder. Associated with this is an increase in the dimethyldichlorosilane yield within the experimental period under consideration. If air is used as the oxidizing agent (Example 3), not only is it impossible to achieve activation, but an additional fall in the catalytic activity of the copper thus oxidized, compared with the original material, results.

If the nitrogen in Example 2 is replaced by carbon monoxide, a typical constituent of combustion gases, and oxidation is carried out under otherwise identical conditions, the selectively and dimethyldichlorosilane yield of the catalysts then obtained fall below the level for the starting material (Example 4).

In Example 5 and 6, Cu powders are oxidized at high temperatures with short residence times and, respectively, under a greatly reduced partial pressure of oxygen.

EXAMPLE 1

A cylindrical V2A tube of 600 mm height and 30 mm internal diameter which is provided with a thermocouple and a perforated tray and into which a blade stirrer made of the same material dips such that the stirring movements take place directly above the perforated tray, is used as the stirred bed reactor. The perforated tray fitted into the cylindrical V2A tube consists of two circular V2A discs riveted onto one another, each having 39 equidistant openings of 1 mm diameter, in each case opposite to one another. Between the two discs is a V2A gauze of 0.05 mm mesh width, which is inserted between the two discs before they are riveted together and prevents the Cu powder from falling through. The reactor is sealed from the atmosphere at the head by a lid, in which the stirrer guide (stuffing box) is located. A tube of about 5 mm diameter at the reactor head enables the reaction gases to leave the reactor, these passing through a filter.

The gas is metered in by means of a calibrated flow meter. The gas mixture enters the reactor below the perforated tray. A layer of quartz wool below the perforated tray prevents any solid from passing through during standstill. The stirred bed is surrounded by an electrically heatable oven, the temperature of which can be controlled.

30 g of a commercially available copper powder, prepared by mechanical comminution of copper, having a particle size of 0.1 to 10 microns, a surface area, measured by the BET method, of 1.5 m²/g and an oxygen content of 2.0% are initially introduced into the reaction vessel and are oxidized at 200° C. for 10 minutes with 50 Nl/hour of a gas mixture containing 0.7% by volume of $O_2$ and 99.3% by volume of $N_2$. The oxygen content of the powder thereby rises to 2.2%.

The activity of the catalyst prepared by the process according to the invention is compared with that of the non-treated material in the following table, the testing of both Cu powders having taken place in the above-mentioned laboratory fixed bed reactor under identical conditions.

Table Ib shows the test results of two commercially available types of catalyst.

Table Ia

| Original copper powder Hours after the start-up of the reaction | 1 | 2 | 3 | 4 | 5 | 6 | 7 | ε |
|---|---|---|---|---|---|---|---|---|
| Temperature °C. | 350 | 340 | 325 | 310 | 295 | 280 | 280 | |
| Crude silane yield, g of silane/hour | 1.55 | 1.82 | 1.88 | 1.87 | 1.84 | 1.54 | 1.19 | 11.7 |
| $(CH_3)_2SiCl_2$ in the crude silane, % by weight | 47.8 | 48.9 | 49.2 | 63.5 | 75.7 | 81.3 | 84.6 | |
| $CH_3SiCl_3$ in the crude silane, % by weight | 36.5 | 35.4 | 32.5 | 24.1 | 15.9 | 12.5 | 10.4 | |
| $(CH_3)_2SiCl_2$ yield, g of $(CH_3)_2SiCl_2$/hour | 0.74 | 0.89 | 0.92 | 1.19 | 1.39 | 1.25 | 1.01 | 7.4 |
| Oxidized copper powder Hours after the start-up of the reaction | 1 | 2 | 3 | 4 | 5 | 6 | 7 | ε |
| Temperature °C. | 350 | 340 | 325 | 310 | 295 | 280 | 280 | |
| Crude silane yield, g of silane/hour | 1.70 | 2.03 | 1.98 | 1.19 | 1.93 | 1.68 | 1.54 | 12.8 |
| $(CH_3)_2SiCl_2$ in the crude silane, % by weight | 53.3 | 56.4 | 57.2 | 74.9 | 82.0 | 86.4 | 87.0 | |
| $CH_3SiCl_3$ in the crude silane, % by weight | 36.0 | 32.7 | 27.2 | 16.3 | 11.2 | 8.5 | 8.0 | |
| $(CH_3)_2SiCl_2$ yield, g of $(CH_3)_2SiCl_2$/hour | 0.91 | 1.14 | 1.13 | 1.43 | 1.58 | 1.45 | 1.34 | 9.0 |

Table Ib

| Commercially available copper catalysts (Manufacturer: Messrs. Pitt Metals, Batch 50) Hours after the start-up of the reaction | 1 | 2 | 3 | 4 | 5 | 6 | 7 | ε |
|---|---|---|---|---|---|---|---|---|
| Temperature °C. | 350 | 340 | 325 | 310 | 295 | 280 | 280 | |
| Crude silane yield, g of silane/hour | 1.67 | 1.70 | 1.79 | 1.61 | 1.38 | 0.99 | 0.76 | 9.9 |

Table Ib-continued

| | | | | | | | | |
|---|---|---|---|---|---|---|---|---|
| $(CH_3)_2SiCl_2$ in the crude silane, % by weight | 29.6 | 39.0 | 48.9 | 60.7 | 69.1 | 74.9 | 78.4 | |
| $CH_3SiCl_3$ in the crude silane, % by weight | 54.9 | 47.8 | 40.9 | 32.8 | 26.2 | 19.7 | 15.7 | |
| $(CH_3)_2SiCl_2$ yield, g of $(CH_3)_2SiCl_2$/hour | 0.49 | 0.66 | 0.88 | 0.98 | 0.95 | 0.74 | 0.60 | 5.3 |

Commercially available copper catalysts
(Manufacturer: Messrs. Chemet, Batch 10)

| Hours after the start-up of the reaction | 1 | 2 | 3 | 4 | 5 | 6 | 7 | ε |
|---|---|---|---|---|---|---|---|---|
| Temperature °C. | 350 | 340 | 325 | 310 | 295 | 280 | 280 | |
| Crude silane yield, g of silane/hour | 1.78 | 1.97 | 1.84 | 1.66 | 1.61 | 1.12 | 0.94 | 10.9 |
| $(CH_3)_2SiCl_2$ in the crude silane, % by weight | 42.5 | 52.4 | 56.1 | 63.3 | 69.2 | 76.9 | 80.2 | |
| $CH_3SiCl_3$ in the crude silane, % by weight | 40.0 | 31.1 | 29.1 | 24.5 | 21.8 | 16.4 | 14.5 | |
| $(CH_3)_2SiCl_2$ yield, g of $(CH_3)_2SiCl_2$/hour | 0.76 | 1.03 | 1.03 | 1.05 | 1.11 | 0.86 | 0.75 | 6.6 |

EXAMPLE 2

30 g of the Cu powder used in Example 1 are after-treated, in the apparatus described therein, at 200° C. for 20 minutes with 50 Nl/hour of a gas mixture consisting of 2% by volume of $O_2$ and 98% by volume of $N_2$. The oxygen content of the reaction product is 2.6%.

In the laboratory reactor, the catalyst obtained subsequently shows the following properties, under the same test conditions as the catalyst produced in Example 1:

Table II

| Hours after the start-up of the reaction | 1 | 2 | 3 | 4 | 5 | 6 | 7 | ε |
|---|---|---|---|---|---|---|---|---|
| Temperature °C. | 350 | 340 | 325 | 310 | 295 | 280 | 280 | |
| Crude silane yield, g of silane/hour | 1.65 | 1.88 | 1.75 | 1.75 | 1.55 | 1.37 | 1.13 | 10.9 |
| $(CH_3)_2SiCl_2$ in the crude silane, % by weight | 50.7 | 55.1 | 62.7 | 72.8 | 78.9 | 84.3 | 86.2 | |
| $CH_3SiCl_3$ in the crude silane, % by weight | 34.5 | 28.8 | 22.2 | 15.2 | 12.3 | 9.4 | 8.4 | |
| $(CH_3)_2SiCl_2$ yield, g of $(CH_3)_2SiCl_2$/hour | 0.84 | 1.04 | 1.10 | 1.27 | 1.22 | 1.15 | 0.97 | 7.6 |

EXAMPLE 3

30 g of the copper employed in Example 1 and 2 are introduced into the same after-oxidation installation and reacted with 50 Nl/hour of air at 200° C. for 20 minutes. The after-oxidized powder contains 13.6% of oxygen. Table III shows that when the resulting product is employed in the test reactor, the catalytic activity falls to below that of the starting material.

Table III

| Hours after the start-up of the reaction | 1 | 2 | 3 | 4 | 5 | 6 | 7 | ε |
|---|---|---|---|---|---|---|---|---|
| Temperature °C. | 350 | 340 | 325 | 310 | 295 | 280 | 280 | |
| Crude silane yield, g of silane/hour | 1.08 | 1.52 | 1.63 | 1.43 | 1.26 | 1.10 | 0.87 | 8.9 |
| $(CH_3)_2SiCl_2$ in the crude silane, % by weight | 48.8 | 54.7 | 57.7 | 63.3 | 71.8 | 78.4 | 82.6 | |
| $CH_3SiCl_3$ in the crude silane, % by weight | 35.5 | 28.1 | 23.8 | 20.0 | 15.9 | 12.3 | 10.8 | |
| $(CH_3)_2SiCl_2$ yield, g of $(CH_3)_2SiCl_2$/hour | 0.53 | 0.83 | 0.94 | 0.91 | 0.90 | 0.86 | 0.72 | 6.2 |

EXAMPLE 4

30 g of the powder used in Example 1 to 3 are oxidized in the known apparatus at 200° C. for 20 minutes with 50 Nl/hour of a gas mixture containing 2% by volume of $O_2$, 8% by volume of $N_2$ and 90% by volume of CO. The oxygen content of the copper is increased to 2.1% by the oxidation. Testing of the resulting catalyst in the laboratory under the same conditions as above shows that the selectivity has been impaired.

Table IV

| Hours after the start-up of the reaction | 1 | 2 | 3 | 4 | 5 | 6 | 7 | ε |
|---|---|---|---|---|---|---|---|---|
| Temperature °C. | 350 | 340 | 325 | 310 | 295 | 280 | 280 | |
| Crude silane yield, g of silane/hour | 1.69 | 1.97 | 1.76 | 1.63 | 1.75 | 1.58 | 1.33 | 11.7 |
| $(CH_3)_2SiCl_2$ in the crude silane, % by weight | 45.9 | 41.2 | 46.6 | 60.6 | 70.0 | 74.5 | 79.8 | |
| $CH_3SiCl_3$ in the crude silane, % by weight | 39.3 | 42.7 | 38.1 | 29.2 | 22.9 | 18.9 | 15.2 | |
| $(CH_3)_2SiCl_2$ yield, g of $(CH_3)_2SiCl_2$/hour | 0.78 | 0.81 | 0.82 | 0.99 | 1.23 | 1.18 | 1.06 | 6.9 |

EXAMPLE 5

50 g of copper powder, the same as was used for Example 1 to 4, are charged, via a metering device, into a vertical tube of 60 mm diameter and 2,000 mm length, which can be heated electrically by 2 fold-open tubular ovens. After the powder has passed the oxidation zone, it passes through a water-cooled cooling zone of 1,000 mm length and is then separated off by means of a downstream cyclone. A glass wool filter at the outlet of the apparatus prevents product which has not been separated off from issuing into the atmosphere.

The gas required for the oxidation and for conveying the solid enters the gravity tube at the head of the installation, through its nozzle above the heating zone. The temperature is measured with thermocouples, around which the gas charged with solid flows.

The after-oxidation takes place at 900° C. with 1 $Nm^3$/hour of a $N_2/O_2$ mixture, the $O_2$ content of which is 6.1%. The reaction product has an oxygen content of 5.8%.

Table V shows the activity of the catalyst thus treated, measured in the laboratory reactor.

Table V

| Hours after the start-up of the reaction | 1 | 2 | 3 | 4 | 5 | 6 | 7 | ε |
|---|---|---|---|---|---|---|---|---|
| Temperature °C. | 350 | 340 | 325 | 310 | 295 | 280 | 280 | |

Table V-continued

| Hours after the start-up of the reaction | 1 | 2 | 3 | 4 | 5 | 6 | 7 | ε |
|---|---|---|---|---|---|---|---|---|
| Crude silane yield, g of silane/hour | 1.87 | 1.99 | 2.12 | 2.71 | 2.20 | 1.82 | 1.58 | 14.3 |
| $(CH_3)_2SiCl_2$ in the crude silane, % by weight | 41.9 | 45.8 | 51.7 | 65.0 | 71.4 | 76.2 | 80.0 | |
| $CH_3SiCl_3$ in the crude silane, % by weight | 42.4 | 38.2 | 32.7 | 24.7 | 19.9 | 16.4 | 13.7 | |
| $(CH_3)_2SiCl_2$ yield, g of $(CH_3)_2SiCl_2$/hour | 0.78 | 0.91 | 1.10 | 1.76 | 1.57 | 1.39 | 1.26 | 8.8 |

EXAMPLE 6

30 g of a metal powder, produced by atomization of a copper melt, which has a particle size of 10–100 microns, a surface area, measured by the BET method, of 0.4 m²/g and an oxygen content of 0.4% are oxidized, in the apparatus described in Example 1, with 400 Nml $O_2$/hour at 600° C. for 40 minutes. The procedure here is to continuously suck off the oxygen entering into the reaction chamber so that a pressure of 0.004 atmospheres absolute is set up therein during the oxidation period. The powder thus treated contains 0.8% of oxygen.

The resulting product is tested in the manner described. Table VI compares the catalytic properties of the starting material with those of the after-treated powder.

Table VI

| Original copper powder<br>Hours after the start-up of the reaction | 1 | 2 | 3 | 4 | 5 | 6 | 7 | ε |
|---|---|---|---|---|---|---|---|---|
| Temperature °C. | 350 | 340 | 325 | 310 | 295 | 280 | 280 | |
| Crude silane yield, g of silane/hour | 1.41 | 1.42 | 1.21 | 0.60 | 0.32 | 0.17 | 0.07 | 5.2 |
| $(CH_3)_2SiCl_2$ in the crude silane, % by weight | 36.5 | 31.3 | 41.6 | 46.2 | 52.5 | 60.1 | 73.5 | |
| $CH_3SiCl_3$ in the crude silane, % by weight | 53.1 | 49.4 | 49.9 | 48.0 | 43.3 | 36.6 | 23.1 | |
| $(CH_3)_2SiCl_2$ yield, g of $(CH_3)_2SiCl_2$/hour | 0.51 | 0.44 | 0.50 | 0.28 | 0.17 | 0.10 | 0.05 | 2.1 |
| Oxidized copper<br>Hours after the start-up of the reaction | 1 | 2 | 3 | 4 | 5 | 6 | 7 | ε |
| Temperature °C. | 350 | 340 | 325 | 310 | 295 | 280 | 280 | |
| Crude silane yield, g of silane/hour | 1.52 | 1.60 | 1.56 | 1.13 | 0.65 | 0.66 | 0.18 | 7.3 |
| $(CH_3)_2SiCl_2$ in the crude silane, % by weight | 41.3 | 60.4 | 70.3 | 79.4 | 83.8 | 85.4 | 84.3 | |
| $CH_3SiCl_3$ in the crude silane, % by weight | 43.9 | 26.1 | 18.9 | 12.8 | 10.5 | 10.7 | 11.3 | |
| $(CH_3)_2SiCl_2$ yield, g/hour | 0.63 | 0.97 | 1.10 | 0.90 | 0.54 | 0.56 | 0.15 | 4.9 |

It will be appreciated that the instant specification and examples are set forth by way of ilustration and not limitation, and that various modifications and changes may be made without departing from the spirit and scope of the present invention.

What we claim is:

1. In the preparation of catalytic copper with an average particle size between about 0.1 and 100 microns and a copper-I oxide content of about 3 to 100% by oxidation of a Cu powder, the improvement which comprises carrying out the oxidation with oxygen at a reduced partial pressure compared with that of air, the resulting catalyst being of enhanced catalytic activity.

2. A process according to claim 1, wherein the oxygen is mixed with further gases which are either inert or also have an oxidizing action, the oxygen content in the gas mixture being between about 0.1 and 15% by volume.

3. A process according to claim 1, wherein oxygen under a pressure of about 0.001 to 0.2 atmospheres absolute is used as the oxidizing agent.

4. A process according to claim 1, wherein the oxidation is carried out at a temperature between about 100° to 1,000° C.

5. A process according to claim 1, wherein the residence time of the Cu powder in the oxidation zone is between about 2 seconds and 120 minutes.

6. Catalytic copper produced by the process of claim 1.

7. In the reaction of hydrocarbon chlorides with silicon in the presence of a copper catalyst to produce an organochlorosilane, the improvement which comprises employing as said catalyst catalytic copper produced by the process of claim 1, whereby the yield and selectivity of conversion are increased.

* * * * *